(12) United States Patent
Schwarz et al.

(10) Patent No.: US 7,626,060 B2
(45) Date of Patent: Dec. 1, 2009

(54) PROCESS FOR THE PREPARATION OF PHENOLIC COMPOUNDS, FOR SEPARATING PHENOL FROM CLEAVAGE PRODUCT MIXTURES, AND AN APPARATUS

(75) Inventors: Christoph Schwarz, Marl (DE); Markus Weber, Haltern (DE); Manfred Weber, Haltern (DE)

(73) Assignee: INEOS Phenol GmbH & Co., KG, Gladbeck (DE)

( * ) Notice: Subject to any disclaimer, the term of this patent is extended or adjusted under 35 U.S.C. 154(b) by 588 days.

(21) Appl. No.: 10/888,533

(22) Filed: Jul. 9, 2004

(65) Prior Publication Data

US 2005/0034970 A1 Feb. 17, 2005

Related U.S. Application Data

(60) Provisional application No. 60/486,845, filed on Jul. 11, 2003.

(51) Int. Cl.
  *C07C 37/00* (2006.01)
  *C07C 37/68* (2006.01)
(52) U.S. Cl. .................................. 568/741; 568/742
(58) Field of Classification Search ................ 568/741, 568/742
  See application file for complete search history.

(56) References Cited

U.S. PATENT DOCUMENTS 2,663,735 A 12/1953 Filar et al.

(Continued)

FOREIGN PATENT DOCUMENTS

DE 1 105 878 5/1961

(Continued)

OTHER PUBLICATIONS

Olsen et al., (Unit Processes and Principles of Chemical Engineering, 1932, pp. 1-3).*

(Continued)

*Primary Examiner*—Jafar Parsa
(74) *Attorney, Agent, or Firm*—Knobbe, Martens, Olson & Bear, LLP (57) ABSTRACT

To improve energy efficiency of prior art processes while preserving the standards of quality and total yield of desired end products, a process for the preparation of phenolic compounds is proposed. The process of the invention comprises working-up of the cleavage product mixtures by distillation, which comprises resolving the cleavage product mixture into at least three fractions in a single distillation step by feeding the cleavage product mixture to the side of a distillation column, removing a first fraction comprising the ketone at the top of the distillation column, removing a second fraction comprising the phenolic compound at the bottom of the distillation column, and removing a third fraction comprising unreacted the alkylaryl compound and the hydroxy ketone, and water, as side stream, whereby the side stream take-off is situated above the feed of cleavage product mixture to the distillation column, characterized by removing heat from the distillation column, whereby the heat take-off is situated above the side stream take-off of the third fraction, and a process for separating phenol from cleavage product mixtures, wherein the cleavage product mixture prior feeding into the distillation column, is preheated to a temperature of above 70° C. at standard pressure, preferably to a temperature of above 100° C., more preferably to a temperature between 110° C. and 180° C., most preferred to a temperature of about 140° C. to 146° C., and an apparatus suitable therefore.

23 Claims, 6 Drawing Sheets

U.S. PATENT DOCUMENTS

| | | | |
|---|---|---|---|
| 2,757,209 | A | 7/1956 | Joris |
| 3,180,897 | A | 4/1965 | Sodomann et al. |
| 3,322,651 | A | 5/1967 | Nielsen |
| 4,251,325 | A | 2/1981 | Marsh et al. |
| 4,262,150 | A | 4/1981 | Pujado |
| 4,333,801 | A | 6/1982 | Pujado |
| 4,340,447 | A | 7/1982 | Laverick et al. |
| 4,358,618 | A | 11/1982 | Sifniades et al. |
| 4,370,205 | A | 1/1983 | Pujado |
| 5,064,507 | A * | 11/1991 | O'Donnel et al. ............. 203/34 |
| 5,122,234 | A | 6/1992 | Elishewitz et al. |
| 5,131,984 | A | 7/1992 | Chan et al. |
| 5,230,217 | A | 7/1993 | Agrawal et al. |
| 5,254,751 | A | 10/1993 | Zakoshansky |
| 5,463,136 | A | 10/1995 | Blackbourn et al. |
| 5,487,816 | A | 1/1996 | Schulz et al. |
| 5,510,543 | A | 4/1996 | Fulmer et al. |
| 6,225,513 | B1 | 5/2001 | Zakoshansky et al. |
| 6,555,719 | B2 | 4/2003 | Sigg et al. |
| 6,583,326 | B2 * | 6/2003 | Schwarz et al. ............. 568/754 |
| 6,657,087 | B2 | 12/2003 | Weber et al. |
| 2002/0045781 | A1 * | 4/2002 | Tanger et al. ............... 568/385 |

FOREIGN PATENT DOCUMENTS

| | | |
|---|---|---|
| DE | 197 55 026 | 6/1998 |
| DE | 100 21 482 | 11/2001 |
| DE | 100 60 503 | 6/2002 |
| DE | 100 60 505 | 1/2003 |
| EP | 0 032 255 | 7/1981 |
| EP | 1 151 985 | 11/2001 |
| GB | 782865 | 9/1957 |
| GB | 1 021 759 | 3/1966 |
| JP | 61050602 | 3/1986 |
| JP | 200308002 | 3/2003 |
| WO | 02/22532 | 3/2002 |
| WO | WO 02/46132 | 6/2002 |
| WO | WO 02/46133 | 6/2002 |

OTHER PUBLICATIONS

International Search Report from co-pending PCT Application No. PCT/EP2004/007277, filed Mar. 7, 2004, in 4 pages.

Sattler, "Thermische Trennverfahren," *VCH Verlagsgesellschaft*, Weinheim, pp. 140-141, 1988.

International Search Report dated Oct. 11, 2004.

* cited by examiner

PROCESS FOR THE PREPARATION OF PHENOLIC COMPOUNDS, FOR SEPARATING PHENOL FROM CLEAVAGE PRODUCT MIXTURES, AND AN APPARATUS

RELATED APPLICATIONS

This application claims the benefit of U.S. Provisional Application No. 60/486,845, filed Jul. 11, 2003, which is expressly incorporated herein by reference in its entirety.

FIELD OF THE INVENTION

The invention relates to an improved process for the preparation of phenolic compounds, and an improved process for separating phenol from cleavage product mixtures. The invention further relates to an improved apparatus for performing such process.

BACKGROUND OF THE INVENTION

The process of acid-catalyzed cleavage of cumene hydroperoxide into phenol and acetone has been of particular industrial importance for a long time. In the preparation of phenol from an alkylaryl compound like cumene by the Hock process, cumene is oxidized to cumene hydroperoxide (CHP) in a first reaction step, known as the oxidation, and the CHP is subsequently concentrated to from 65 to 90% by weight in a vacuum distillation, known as the concentration. In a second reaction step, known as the cleavage, the CHP is cleaved into a phenolic compound and a ketone by action of an acid, usually sulfuric acid. Apart from phenol as the phenolic compound and acetone as the ketone, the cleavage product further comprises additional compounds which can have been formed in the reaction steps preceding the cleavage and which are only partly transformed, if at all, in the cleavage. The most important compounds that may be present in the cleavage product in addition to phenol and acetone are, in particular, α-methylstyrene (AMS), cumene and acetophenone. In addition, small amounts of dimethyl phenyl carbinol (DMPC) formed in the oxidation can be present in the cleavage product. Further impurities include compounds such as methylbenzofuran (MBF), hydroxy acetone, mesityl oxide (MO) and carbonyl compounds such as acetaldehyde and 2-phenyl-propion-aldehyde. After neutralization of the cleavage product and possible removal of an aqueous phase, the cleavage product is worked up by distillation.

Various processes for working up the cleavage product mixtures by distillation are known (Ullmann's Encyclopedia of Industrial Chemistry, 5th completely revised edition, Vol. A19, 1991, VCH Verlagsgesellschaft mbH, Weinheim). In principle, all these processes involve initial neutralization of the cleavage product mixtures using aqueous sodium hydroxide, amines or aqueous phenoxide solution. After phase separation, the organic part of the neutralized cleavage product mixture is transferred to a first column in which crude acetone is distilled off from the remaining cleavage product via the top of the column. This crude acetone is usually treated with alkali in a scrubber and once again purified by distillation. However, the scrub is sometimes also carried out in the column. The bottom product from the first column is distilled in a second column from which AMS and cumene are taken off at the top and are usually passed to a hydrogenation in which cumene is produced again. AMS and cumene can also be separated off by azeotropic distillation in the presence of water. The bottom product remaining in the second column is distilled in a crude phenol column.

The crude phenol obtained can be purified further by extractive distillation using water or by treatment with an acid ion exchanger and subsequent distillation. In the latter process, compounds that are difficult to separate from phenol by distillation, e.g., mesityl oxide and hydroxy acetone, are condensed to form higher-boiling compounds.

Such a process is described, for example, in U.S. Pat. No. 5,064,507 (assigned to Allied). In this process, the cleavage product is firstly separated from the crude acetone in a crude acetone column. The bottom product is transferred to a cumene column in which cumene and AMS are separated from the cleavage product. The column is, however, operated so that a certain proportion of AMS remains in the bottom product since this is required as reactant or solvent in the further processing of the phenol to remove MBF and other impurities. This bottom product is reacted with an amine, preferably hexamethylenediamine, in a reactor having plug flow characteristics in order to convert carbonyl compounds, e.g., acetol (hydroxy acetone) or MO, into higher-boiling compounds. The product, which has been treated in this way, is worked up further by distillation. However, it needs to pass through further four columns and two reaction zones before the purified end product phenol is obtained. The initial outlay for apparatus required for the removal of the hydroxy acetone from the phenol is relatively high in this process.

According to DE-AS 1 105 878 (Phenolchemie), the neutralized cleavage product which is separated off from the crude acetone in a crude acetone column is transferred into a hydrocarbon column in which, in the presence of water, hydrocarbons boiling lower than phenol, such as AMS and cumene are distilled off overhead. From the bottom of the column the organic phase is taken off and applied to the top of a downstream column in which water is separated off from phenol and high-boilers which are produced in the bottom of the column. The mixture of phenol and high-boilers is then transferred to a crude phenol column. The residues produced in the crude phenol column and in the pure phenol distillation can then be fed to a cracking still in which the residues are worked up and one part of phenol is recovered. These recovered products of value can be transferred again to the hydrocarbon column.

EP 0 032 255 (UOP) describes a process for working up cleavage product in which the organic part of a virtually neutralized (pH≈6) cleavage product is again washed with water and then the organic part is transferred to a crude acetone column in which the crude acetone is separated off from the remaining cleavage product. The residue remaining in the bottom phase is transferred directly to a cumene column in which the crude phenol is produced as bottoms product which in turn is fed to a purifying distillation. The mixture taken off overhead from the cumene column, which contains principally AMS, cumene and water, is transferred to a phase-separation vessel in which an aqueous phase is separated off. The resultant organic phase is transferred to a washing column in which the organic mixture is treated with sodium hydroxide solution in order to remove any phenol still present from the mixture of AMS and cumene as sodium phenoxide. The mixture of AMS and cumene which has been freed from phenol is fed via the top of the column to a hydrogenation.

In U.S. Pat. No. 4,262,150 (UOP), also, the same column circuit is used as described in EP 0 032 255 (UOP). The difference from EP 0 032 255 is that, to neutralize the cleavage product, an extraction column is used instead of one or more combinations of mixers and phase-separation apparatuses.

U.S. Pat. No. 3,322,651 (assigned to UOP), describes the use of nitrogen compounds, in particular amines, for purifying phenol obtained in the cleavage of CHP. However, the amines added likewise have to be removed again from the products and are quite expensive.

U.S. Pat. No. 5,510,543 (GE) describes a process for working up the cleavage product from CHP cleavage, in which the cleavage product is adjusted to a pH of 4.0 to 4.9 in a neutralizer by adding a base, in particular sodium hydroxide solution. In the neutralizer the cleavage product is separated into an aqueous phase and an organic phase. The organic phase is transferred to a column termed the splitter in which the cleavage product is separated by distillation into an acetone-rich fraction and a phenol-rich fraction. The phenol-rich fraction is taken off at the bottom of the column and fed to a phenol purification, which can consist, for example, of one or more further distillations. The acetone-rich fraction is taken off at the top of the column and fed to an acetone column, in which case base is added to this fraction before entry into the column in such an amount that the fraction has a pH of approximately 9, so that the organic acids which are also present in this fraction are neutralized. The mixture arising in the bottom phase of the column which, in addition to water, also contains hydrocarbons and the salts of organic acids, is transferred to a phase-separation apparatus in which this mixture is separated into an organic phase and an aqueous phase. The organic phase can be treated again for recovery of cumene.

Furthermore, processes have been developed in which individual fractions which arise in the work-up by distillation of cleavage product are treated specifically. Thus, U.S. Pat. No. 5,487,816 (UOP) describes a process for separating off AMS from a mixture which contains phenol, AMS and water and which arises as bottom product of a crude acetone column. The crude acetone column is operated in this case in such a manner that cumene is taken off from the cleavage product at the top of the crude acetone column together with the acetone. The mixture containing AMS and phenol is separated in a column in such a manner that in the bottom of the column predominantly phenol is produced, which can be fed to further work-up, and at the top of the column a mixture of AMS, water and smaller amounts of phenol is taken off, which mixture is condensed and adjusted to a pH above 6 by adding a basic reagent. This achieves the phenol being principally present in the aqueous phase, while the AMS is present in an organic phase in which only small amounts of phenol are present as impurity. The phases are separated from one another by a phase-separation apparatus. The organic phase can be fed to a hydrogenation, while the aqueous phase can be fed back to the column as reflux.

In U.S. Pat. No. 4,370,205 (UOP), the stream taken off from the bottom of the crude acetone column also still contains cumene, in contrast to the process described in U.S. Pat. No. 5,487,816 (UOP). Against this background a different column circuit is proposed. In particular two columns operated under virtually the same conditions are used in which the bottoms product produced is predominantly phenol, whereas predominantly AMS and cumene are taken off overhead. The crude phenol taken off as bottoms product in the first column is fed to further work-up steps, and the crude phenol taken off as bottoms product in the second column is fed back to the first column. The overhead product of the second column is treated with sodium hydroxide solution in a wash column. The overhead product of this column, which comprises AMS and cumene, can be fed to the hydrogenation.

GB 1 021 759 (Mitsui) describes the work-up of a cleavage product mixture, which has been obtained in the acid-catalyzed cleavage of CHP and from which the catalyst has been removed by neutralization and scrubbing. To be able to obtain a phenol having a low hydroxy acetone content, the separation is carried out by feeding the cleavage product mixture into a distillation column at a side inlet and fractionating this mixture in one separation step to give a top fraction comprising water, acetone, hydroxy acetone and cumene and a bottom fraction comprising phenol having a hydroxy acetone content of less than 100 ppm. Depending on the composition of the cleavage product mixture, cumene was added in an amount so that the ratio of cumene to phenol in the feed to the column was at least 0.28 part by weight of cumene to 1 part by weight of phenol, since the process is based on the separation of an azeotropic mixture of hydroxy acetone and cumene from the phenol. The hydroxy acetone can be removed from the phenol by this process. However, a top fraction that comprises not only water, cumene and hydroxy acetone but also acetone is obtained. Phenol contamination may also be present in the top fraction. These products likewise have to be separated from one another.

In U.S. Pat. No. 4,251,325 (assigned to BP Chemicals), the work-up of a fraction which has been substantially freed of low boilers, water, and acetone has been optimized by operating the cumene column in such a way that a mixture comprising cumene, AMS and hydroxy acetone is taken off at the top, with this mixture being separated virtually completely from the crude phenol remaining in the bottoms and thus not having to be removed in a costly fashion during the work-up of the phenol. This process gives phenol containing less than 30 ppm of hydroxy acetone. A disadvantage of this process is the fact that the input mixture has to be substantially freed of water, which is why an acetone fraction comprising low boilers and also the major part of the water present in the cleavage product mixture has to be separated from the cleavage product mixture in the preceding separation step. The work-up of such an acetone fraction by methods of the prior art is relatively uneconomical, since a high expenditure for apparatus is required.

U.S. Pat. No. 4,333,801 (UOP) describes the work-up of a fraction which comprises AMS, cumene, phenol, water and impurities, for example hydroxyacetone. This process is chiefly concerned with removing an AMS/cumene fraction, which has a very low phenol concentration, from the total fraction. This is achieved by operating the cumene column in such a manner that a mixture of cumene and AMS is taken off overhead from the column, which mixture is condensed and run into a phase-separation vessel. Any water possibly present is separated off and discarded. A portion of the organic phase is fed back to the column top as reflux. Another portion of the organic phase is fed to a washer in which phenol residues which would interfere with the hydrogenation are removed from the phase so that this phase can be fed to the hydrogenation. From a side stream takeoff of the cumene column there is taken off a fraction comprising AMS and cumene and an azeotropic mixture of water and phenol, which fraction is also condensed and transferred to a phase-separation vessel. The aqueous phase which can comprise phenol is fed to a work-up stage. The organic phase which comprises cumene, AMS and as much phenol as remains in the organic phase in accordance with the phase equilibrium between the organic and aqueous phases is evaporated and fed back in the vaporous state into the cumene column above the side stream takeoff. A crude phenol fraction is taken off from the bottom of the column.

A process for phenol rectification with energy recovery has been described in U.S. Pat. No. 5,131,984, however, the crude phenol feed has to be freed from substantial portions of acetone, cumene and AMS by conventional process, thus limiting the overall energy recovery possibilities.

A similar process is described in U.S. Pat. No. 5,122,234 (Allied) with the difference that water is additionally run into the column and at the top of the column a mixture which predominantly comprises water and phenol is taken off, which mixture is partly condensed and returned to the column.

U.S. Pat. No. 4,340,447 describe a process and apparatus for obtaining pure acetone from CHP cleavage reaction product.

From DE 100 60 505 A1 and WO 02/46133 A1, and DE 100 60 503 A1 and WO 02/46132 A1, the disclosure of which is hereby incorporated by reference, a process is known for separating phenol from a mixture comprising at least cumene, phenol and hydroxy acetone, in which process a phenol having a hydroxy acetone content of less than 30 ppm is separated from the mixture with comparatively low energy consumption, with a low outlay in terms of apparatus and in the presence of water. It is stated there that a mixture comprising at least phenol, water, hydroxy acetone and cumene can be worked up by means of a single fractional distillation step with subsequent phase separation to give phenol having a hydroxy acetone content of less than 30 ppm, with this fractional distillation step being able to be carried out with a lower energy consumption and a lower outlay in terms of apparatus than in conventional processes. Likewise, it is described that reversal of the order of the process steps also enables phenol having a hydroxy acetone content of less than 30 ppm to be separated from the abovementioned mixture.

SUMMARY OF THE INVENTION

Accordingly a process is proposed for separating phenol from a mixture comprising at least hydroxy acetone, cumene, water and phenol, which comprises fractionating the mixture by means of at least one fractional distillation step and at least one phase separation step in such a way that at least one phenol-containing fraction containing less than 300 ppm of hydroxy acetone is obtained.

Further, an apparatus is proposed in DE 100 60 505 A1 and WO 02/46133 A1 for separating phenol from a mixture comprising at least hydroxy acetone, cumene, water and phenol, which comprises at least one distillation column which is dimensioned so that an at least cumene- and/or α-methylstyrene-containing fraction can be taken off at the top of the column and a phenol-containing fraction having a hydroxy acetone content of less than 300 ppm can be taken off at the bottom of the column and at least one phase separation apparatus for separating organic phases from aqueous phases.

The advantage of the process described is that the separation step chosen in the distillation substantially simplifies the further work-up of the cleavage product mixture or of the individual fractions obtained from the cleavage product mixture. In particular, the joint removal of hydroxy acetone, AMS and cumene from the phenol-containing remainder of the cleavage product mixture substantially simplifies the work-up of the phenol-containing fraction, since the steps carried out in conventional processes in which the hydroxy acetone remains in the phenol-rich fraction and is removed therefrom by reacting the hydroxy acetone with phenol to form compounds which have a boiling point higher than that of phenol and can be separated from the phenol by distillation become unnecessary.

Compared to the earlier conventional processes, the proposed process has a significantly more favorable energy balance and also gives a higher total yield of phenol, based on the phenol content of the cleavage product mixture. The proposed apparatus is significantly simplified, since both the number of distillation columns required and also the number of reaction apparatuses necessary for reducing the contents of the various by-products in the fractions are reduced.

DETAILED DESCRIPTION OF THE PREFERRED EMBODIMENT

Although the process and apparatus of DE 100 60 505 A1 and WO 02/46133 A1 provides significant innovation with respect to earlier known processes and apparatus and improvement of both efficiency as well as energy consumption, and further, less monetary capital needs to be invested for machinery than in the past, however, energetic efficiency is still an issue and there is a ongoing need to cut production costs without affecting the quality of products.

It is therefore an object of the present invention to further improve energy efficiency of prior art processes while preserving the standards of quality and total yield of desired end products.

These and other objects are achieved by a process for the preparation of phenolic compounds comprising the steps of i) oxidizing an alkylaryl compound to produce a reaction mixture comprising alkylaryl hydroperoxide and the unreacted alkylaryl compound; ii) subjecting the product from step i) to a cleavage reaction resulting in a cleavage product mixture comprising at least the phenolic compound, a ketone, the corresponding hydroxy ketone and the unreacted alkylaryl compound; iii) working-up of the cleavage product mixtures from step ii) by distillation, which comprises separating the cleavage product mixture into at least three fractions in a single distillation step by feeding the cleavage product mixture to a distillation column, removing a first fraction comprising the ketone at the top of the distillation column, removing a second fraction comprising the phenolic compound at the bottom of the distillation column, and removing a third fraction comprising unreacted the alkylaryl compound and the hydroxy ketone as side stream, whereby the side stream take-off is situated above the feed of cleavage product mixture to the distillation column, characterized by removing heat from the distillation column, whereby the heat take-off is situated above the side stream take-off of the third fraction.

With the process of the invention even an highly integrated process as for example known from DE 100 60 505 A1 and WO 02/46133 A1 can be significantly improved with respect to energy consumption and monetary capital investment for apparatus required. The process of the invention provides an internal reflux, thus improving the reflux ratio, whereby the column head for removing the first fraction can be constructed much smaller, and further much smaller condensers are required for removing the first fraction from the cleavage product mixture.

In a most preferred embodiment of the invention the heat removed from the distillation column is used for heating a second distillation column for obtaining purified ketone from the first fraction. In typical industrial applications of the invention no additional heating energy, as steam, is required for heating the bottoms in a second purification column, thus, both saving a significant part of energy lost from the process through cooling as well as the energy for heating the bottoms of a purification column otherwise required.

Particularly, if the heat transfer from the distillation column to the second purification column is performed by drawing vapors from the heat-take-off, delivering the vapors to a condenser located at the bottom of the second column and transferring the heat energy to the bottoms of the second column by condensing the vapors in the condenser, and than returning the condensed liquid to the distillation column, both energy savings and improvement of the internal reflux ration of the distillation column are optimized. Heat transfer may be easily controlled by controlling the amount of vapors drawn from the heat take off. This arrangement allows a small and lightweight column head, thus reducing investment costs as well as maintenance costs as no heat exchanger is located at hardly accessible places, and particularly allowing an inexpensive and strong column design for high wind speeds.

However, it may be advantageous if the bottoms of the second purification column are fed through a heat exchanger located at the heat takeoff of the first column.

A preferred application of the invention is a process, where the cleavage reaction mixture is part of a cleavage product mixture obtained from the acid-catalyzed cleavage of alkylaryl hydroperoxide.

The process of the invention is of important economical value where the alkylaryl compound is cumene, the phenolic compound is phenol, the ketone is acetone, and the hydroxy ketone is hydroxy acetone.

In a suitable embodiment of the process the cleavage product mixture further comprises water.

In a preferred industrial embodiment of the process of the invention the step of removing heat from the distillation column provides a temperature at the column top of less than 65° C., preferably of around 55° C. to 60° C. at standard pressure.

In a further preferred embodiment of the process of the invention the cleavage product mixture prior feeding into the distillation column, is preheated to a temperature of above 70° C. at standard pressure, preferably to a temperature of above 100° C., more preferably to a temperature between 110° C. and 180° C., most preferred to a temperature of about 140° C. to 146° C.

The above and other objects are further achieved by a process for separating phenol from cleavage product mixtures comprising at least acetone, cumene, water and phenol, into at least three fractions in a single distillation step by feeding the cleavage product mixture to a distillation column, removing a first fraction comprising acetone at the top of the distillation column, removing a second fraction comprising substituted or unsubstituted phenol at the bottom of the distillation column, and removing a third fraction comprising optionally hydroxy acetone and cumene as side stream, whereby the side stream take-off is situated above the feed of cleavage product mixture to the distillation column, wherein the cleavage product mixture prior feeding into the distillation column, is preheated to a temperature of above 70° C. at standard pressure, preferably to a temperature of above 100° C., more preferably to a temperature between 110° C. and 180° C., most preferred to a temperature of about 140° C. to 146° C.

The separating process of the invention provides both reduced apparatus requirements as well as improved separation performance compared to the processes known in the art.

In a most preferred embodiment of the invention, the heat energy for the preheating step is obtained from cooling of the cleavage product after thermal after-treatment of the cleavage product from acid-catalyzed cleavage of cumene hydroperoxide, prior to neutralization of the cleavage product mixture.

Such thermal after-treatment is described for instance in DE 100 21 482 A1 and EP 1 151 985 A1. From those prior art documents, hereby incorporated by reference, a process for thermal after-treatment of cleavage product from the acid-catalyzed cleavage of cumene hydroperoxide is known, generally as described above. In the preparation of phenol from cumene by the described Hock process, cumene is oxidized to cumene hydroperoxide (CHP) in a first reaction step, known as oxidation, and the CHP is subsequently concentrated to from 65 to 90% by weight in a vacuum distillation, known as concentration. In a second reaction step, known as cleavage, the CHP is cleaved into phenol and acetone by action of an acid, usually sulfuric acid. In this step, the dimethyl phenyl carbinol (DMPC) formed in the oxidation is partly cleaved in an equilibrium reaction into α-methylstyrene (AMS) and water, while a further part of the DMPC reacts with CHP to form dicumyl peroxide (DCP); the rest remains in the cleavage product. After neutralization of the cleavage product, this product mixture is usually worked up by distillation.

During the cleavage, part of the AMS forms high boilers (dimers, cumylphenols) which are discharged as a residue from the distillation. The AMS still present after the neutralization is hydrogenated to cumene during the distillation and is recirculated to the oxidation. DMPC that has not reacted in the cleavage goes as high boiler to the residue, and part of it reacts further in the hot phenol columns to form AMS from which high-boiling secondary components are in turn formed. The DCP is stable at customary cleavage temperatures (50 to 70° C.). In the hot phenol columns, it decomposes thermally to form by products. On the other hand, in the presence of acid, DCP can be cleaved into phenol, acetone and AMS at temperatures above 80° C. It is therefore advantageous to react the residual DMPC and the DCP formed in the cleavage completely immediately after the cleavage by means of a targeted increase in the temperature in the presence of the acid used as catalyst in the cleavage. In this way, DMPC is converted virtually completely into AMS, and DCP is converted completely into phenol, acetone and likewise AMS.

Such a thermal after-treatment of the cleavage product has already been described in U.S. Pat. No. 2,757,209, where temperatures above 100° C., especially from 110 to 120° C., were used. The aim of this thermal after-treatment was complete dehydration of the DMPC to AMS. In contrast, U.S. Pat. No. 4,358,618 describes a thermal after-treatment which has as its aim the complete conversion of the DCP formed in the cleavage into phenol, acetone and AMS, using temperatures of from 120 to 150° C. U.S. Pat. No. 5,254,751 describes a thermal after-treatment with the same objective as in U.S. Pat. No. 4,358,618, using temperatures of from 80 to 110° C. Finally, in DE 197 55 026 A1, the after-treatment is carried out in a temperature range above 150° C. Accordingly, the optimum temperature ranges specified for the thermal after-treatment of cleavage product from phenol production differ widely in the disclosures hitherto.

In the disclosure of U.S. Pat. No. 5,463,136 it is pointed out that an effective cooling, and particularly, temperature control is required to inhibit reaction in the transport lines to avoid forming of bubbles and vapor which would cavitate the transportation pump and therefore causing a general failure of the process. Further, effective cooling is required as a first step to stop the reaction, prior to neutralizing the reaction product. U.S. Pat. No. 2,663,735 proposes removing of the reaction heat by acetone evaporation and controlling the temperature by feeding acetone to the reactor as an alternative to the use of cooling water.

In all these previously described processes, the cleavage product is firstly heated by means of steam in heat exchangers for the thermal after-treatment and, after a sufficient reaction time, is cooled again by means of water in heat exchangers. Depending on the temperature selected for the thermal after-treatment, this requires significant amounts of steam and cooling water. We have found that increased deposition of high-boiling by-products in the heat exchangers (fouling) of the thermal after-treatment generally occurs at above 100° C., especially above 120° C., and this is associated with a drastic decrease in heat transfer. Particularly in the apparatuses for heating the product by means of steam, there is formation of organic deposits on the hot heat exchange surfaces on the product side, so that these apparatuses have to be cleaned at relatively short intervals of a few weeks. This fouling increases further as the temperatures increases.

DE 100 21 482 A1 and EP 1 151 985 A1 therefore propose a process for the thermal after-treatment of cleavage product from cumene hydroperoxide cleavage, which shows not only high selectivity but also low energy costs and a high availability due to avoidance of fouling. Such a process for the thermal after-treatment of cleavage product from the acid-catalyzed cleavage of cumene hydroperoxide into phenol and acetone in which the cleavage product to be treated thermally is heated in a reactor and in which the heat of reaction of at least one exothermic reaction occurring in this reactor is utilized for heating the cleavage product to be treated thermally in the reactor achieves a high selectivity of the after-treatment combined with a lowering of the energy costs and a higher operating period of the heat exchangers due to the avoidance of fouling. The process of DE 100 21 482 A1 and EP 1 151 985 A1 is provided for the thermal after-treatment of cleavage product from the acid-catalyzed cleavage of cumene hydroperoxide into phenol and acetone, in which the cleavage product to be treated thermally is heated in a reactor, wherein the heat of reaction of at least one exothermic reaction occurring in this reactor is utilized for heating the cleavage product to be treated thermally in the reactor.

Likewise, a reactor is proposed for preparing phenol and acetone by acid-catalyzed cleavage of cumene hydroperoxide, which has at least two regions of which at least one region is equipped with an apparatus for removing heat and at least one further region has plug flow characteristics. The apparatus described has the advantage that the actual CHP cleavage and the thermal after-treatment can be combined in one reactor, the description of which is hereby incorporated by reference. The process of DE 100 21 482 A1 and EP 1 151 985 A1 has the advantage that, compared to earlier conventional processes, significantly less steam is required for heating the cleavage product to be subjected to thermal after-treatment. If the heat of reaction liberated in the thermal after-treatment of the cleavage product is sufficient, the use of steam for heating the cleavage product can be omitted entirely. In contrast to processes or other apparatuses in which steam or other suitable heat transfer media are continually used for heating the cleavage product, fouling occurs to a significantly lesser extent or not at all when using the process of the invention for treating the cleavage product.

In a preferred embodiment of a process of the invention the first fraction comprises at least 75% of a ketone present in the cleavage product before the distillation step.

In a particularly useful embodiment of the process of the invention at least one phenol-containing fraction is obtained containing less than 300 ppm, preferably less than 30 ppm, of hydroxy acetone.

Preferably, a further fraction is obtained comprising at least hydroxy acetone, cumene and water and the latter fraction is separated into an organic phase and an aqueous phase. Preferably, the organic and/or the aqueous phase are returned to the column at least partially.

In a useful embodiment of the process of the invention the cleavage product mixture comprises α-methylstyrene, and/or the cleavage product mixture has a phenol concentration of from 20 to 90% by weight.

Preferably, in the process of the invention the cleavage product mixture has a hydroxy acetone concentration of from 300 ppm to 5% by weight.

The process of the invention can be used for an improved process for preparing phenol including the work-up by distillation of mixtures obtained as part of the cleavage product mixtures in the cleavage of cumene hydroperoxide (CHP) into acetone and phenol with subsequent work-up of the cleavage product mixture. The process of the invention is preferably used for separating phenols from a mixture, which comprises at least acetone, cumene, water and phenol and is the cleavage product mixture from the cleavage of CHP.

The above and other objects are further achieved by an apparatus for separating phenol from a mixture comprising at least acetone, cumene, water and phenol, comprising at least one distillation column which is dimensioned such that at least one cumene- and/or α-methylstyrene-containing fraction can be taken off at a side off take of the column located above a side inlet for feeding the cleavage product mixture and a phenol-containing fraction having a hydroxy acetone content of less than 300 ppm can be taken off at the bottom of the column and an off take at the top of the column for removing a first fraction comprising acetone, characterized in that the distillation column further comprises an intermediate heat exchanger or side off take for condensation located above the side off take and below the top of the column.

The apparatus of the invention requires significant lower expenditures for construction compared to those previously proposed as a much smaller column head is required and less expensive condensers provide for removing the first fraction from the mixture with at least a similar separation performance. As the intermediate heat exchanger probably improves the internal reflux ratio of the column, also improved separation performance can be expected.

In a useful embodiment the apparatus of the invention further comprises at least one phase separation apparatus for separating organic phases from aqueous phases.

In a preferred embodiment of the apparatus of the invention the column has at least 20 trays.

The bottom of an apparatus according to the invention can be further simplified by a preheater located upstream of the side inlet in close proximity to the column for preheating the cleavage product mixture prior entry into the column.

In a useful embodiment of the invention the apparatus is characterized in that the preheater is in heat transfer fluid connection with a heat exchanger downstream of a thermal after-treatment reactor outlet. This embodiment allows the use of the cooling water or steam generated from cooling of the after-treatment products for preheating the feed of the column, thus, both saving the need of dumping the heat from the cooling water and the need for thermal energy otherwise provided for correspondingly heating of the column feed.

In a most preferred embodiment of the invention is characterized in that a heat exchanger downstream of a thermal after-treatment reactor outlet forms a preheater located upstream of the side inlet of the column. Thus, the cleavage product mixture, after being cooled down for neutralization and intermediate storage for removal of salts, is fed through the heat exchanger downstream of a thermal after-treatment reactor outlet, and subsequently into the distillation column. Thus, the neutralized cleavage product mixture forms a cooling medium for the cleavage product mixture before neutralization and is preheated at the same time to approximately the temperature associated with the thermal after-treatment of the cleavage product from the acid-catalyzed cleavage of cumene hydroperoxide. Therefore, huge amounts both of cooling water and heating energy can be saved, significantly improving the cost effectiveness of the use of an apparatus according to the invention over those of the prior art.

The process and apparatus of the invention are described below by way of example for the work-up by distillation of a mixture obtained in the acid-catalyzed homogeneous cleavage of CHP and subsequent work-up of the cleavage product mixture, without the process being restricted to this embodiment. This mixture is obtained as part of the cleavage product mixture by separating a crude acetone fraction from the cleavage product mixture.

The process of the invention for separating phenol from a mixture comprising at least acetone, cumene, water and/or hydroxy acetone and phenol comprises fractionating the mixture by means of at least one fractional distillation step and optionally at least one phase separation step such that at least one phenol-containing fraction preferably containing less than 300 ppm of hydroxy acetone is obtained. This phenol-containing fraction is preferably obtained by a process in which a single fractional distillation step and optionally a single phase separation step are carried out.

Before the phenol is separated off, the mixture preferably has a phenol concentration of from 20 to 90% by weight, particularly preferably from 40 to 70% by weight. The mixture can have a hydroxy acetone concentration of from 300 ppm to 5% by weight.

Apart from the compounds mentioned, the mixture may further comprise additional compounds such as α-methylstyrene (AMS), cumene, water, phenylbutenes, methyl-benzofuran (MBF), dimethyl phenyl carbinol (DMPC), cresols, e.g. o-cresol, mesityl oxide (MO), n-propyl-benzene, isopropylphenol, carbonyl compounds such as 3-methylcyclopentenone, (methyl) isobutyl ketones or 2-phenylpropionaldehyde, sec-butylbenzene, tert-butyl-benzene, methylbenzenes, e.g. dimethyl-benzene, acetophenone (AP), ketones, acids, or aldehydes.

The process of the invention can be carried out in different variants, but all of these comprise at least one distillation step.

In an embodiment of the process of the invention, the mixture is fractionated in at least one fractional distillation step, preferably in only a single distillation step, such that a first fraction comprising acetone, a second phenol-containing fraction containing preferably less than 300 ppm of hydroxy acetone, and a third fraction comprising at least hydroxy acetone, cumene and water, are obtained and the latter fraction is separated into an organic phase and an aqueous phase in a phase separation step.

In this embodiment of the process of the invention, the mixture from which phenol is to be separated is firstly fed into a distillation apparatus, preferably a distillation column. The distillation column has to be configured so that it is possible to fractionate the mixture to give at least one acetone comprising fraction, one phenol-containing fraction and at least one further fraction comprising at least cumene, water and hydroxy acetone. The mixture is preferably fed into the column at a side inlet, preferably in a position at which the column has a separation potential of from 25 to 85%, particularly preferably from 40 to 60%. The column is operated so that a phenol-containing fraction can be taken off in liquid form at the bottom of the column. The phenol-containing fraction, which is separated off at the bottom of the column and preferably has a hydroxy acetone concentration of less than 300 ppm is preferably passed as crude phenol to further work-up.

The temperature at the bottom of the column is preferably from 120 to 230° C., particularly preferably from 180 to 195° C. The temperature at the top of the column is preferably less than 65° C., particularly preferably around 55° C. to 60° C. at standard pressure. The temperature at the top of the column is always selected so that the temperature at the top is lower than the temperature at the bottom. The pressure in the column can be from 0.1 to 4 bar. The distillation column is preferably under atmospheric pressure. The desired temperature at the top of the column is obtained by removing heat from the distillation column through a heat exchanger within the column.

In the embodiment of the process of the invention a third fraction comprising unreacted the alkylaryl compound (cumene) and the hydroxy acetone is removed as side stream, whereby the side stream take-off is situated above the feed of cleavage product mixture to the distillation column, and the heat take-off is situated above the side stream take-off of the third fraction. The side stream offtake is suitably located above the feed point for the mixture.

Alternatively or in addition the cleavage product mixture prior feeding into the distillation column, is preheated to a temperature of above 70° C. at standard pressure, preferably to a temperature of above 100° C., more preferably to a temperature between 110° C. and 180° C., most preferred to a temperature of about 140° C. to 146° C., to reduce the energy needed for heating the bottoms in the column.

Most preferred is that the heat energy for the preheating step is obtained from cooling of the cleavage product after thermal after-treatment of the cleavage product from acid-catalyzed cleavage of cumene hydroperoxide. Such product needs to be cooled from about 150° C. to approximately 40° C. to inhibit further uncontrolled reaction of the cleavage product mixture prior neutralization, In the embodiments of the process of the invention, the phenol obtained from the feed mixture preferably not only contains less than 300 ppm of hydroxy acetone, preferably less than 30 ppm, but is also depleted in impurities such as phenylbutenes, methylbenzofuran (MBF), mesityl oxide (MO), n-propyl-benzene, isopropylphenol, carbonyl compounds such as 3-methylcyclopentenone, (methyl) isobutyl ketones or 2-phenylpropionaldehyde, sec-butylbenzene, tert-butyl-benzene or methylbenzenes, e.g. dimethylbenzene. These impurities are separated from the mixture together with α-methylstyrene (AMS), cumene and water via the side stream offtake of the distillation column.

The fractions obtained according to the invention can be worked up further by methods known from the prior art.

The process of the invention for separating phenol from cleavage product mixtures comprising at least hydroxy acetone, cumene, water and phenol is preferably carried out in an apparatus according to the invention.

This apparatus for separating phenol from a mixture comprising at least acetone, cumene, water and phenol, comprising at least one distillation column which is dimensioned such that at least one cumene- and/or α-methylstyrene-containing fraction can be taken off at a side offtake of the column located above a side inlet for feeding the cleavage product mixture and a phenol-containing fraction having a hydroxy acetone content of less than 300 ppm can be taken off at the bottom of the column and an offtake at the top of the column for removing a first fraction comprising acetone, and the distillation column further comprises an intermediate heat exchanger located above the side offtake. Preferably the apparatus further comprises at least one phase separation apparatus for separating organic phases from aqueous phases.

Preferably, a preheater is located upstream of the side inlet in close proximity to the column for preheating the cleavage product mixture prior entry into the distillation column.

According to the invention the preheater is in heat transfer fluid connection with a heat exchanger downstream of a thermal after-treatment reactor outlet. This embodiment allows the use of the cooling water or steam generated from cooling of the after-treatment products for preheating the feed of the column, thus, both saving the need of dumping the heat from the cooling water and thermal energy otherwise provided for correspondingly heating of the column feed.

However, in a most preferred embodiment of the invention a heat exchanger downstream of a thermal after-treatment reactor outlet forms a preheater located upstream of the side inlet of the column. Thus, the cleavage product mixture, after being cooled down for neutralization and intermediate storage for removal of salts, is fed through the heat exchanger downstream of a thermal after-treatment reactor outlet, and subsequently into the distillation column. Thus, the neutralized cleavage product mixture forms a cooling medium for the cleavage product mixture before neutralization and is preheated at the same time to approximately the temperature associated with the thermal after-treatment of the cleavage product from the acid-catalyzed cleavage of cumene hydroperoxide. Therefore, huge amounts both of cooling water and heating energy can be saved, significantly improving the cost effectiveness of the use of an apparatus according to the invention over those of the prior art.

The distillation column preferably has at least 20, more preferably from 40 to 100, theoretical plates or trays. In a particularly preferred embodiment of the apparatus of the invention, it has a side offtake at which a fraction comprising at least one organic acid can be taken off located between the feed point for the mixture and the bottom of the column. The organic acid present in the fraction can be, for example, acetic acid, oxalic acid, formic acid or butyric acid or a mixture comprising at least one of these acids.

As phase separation apparatus, the apparatus of the invention preferably has at least one decanter.

Phenol is obtainable by the process of the invention. This phenol preferably has a hydroxy acetone content of less than 300 ppm, particularly preferably less than 30 ppm. A cumene- and/or AMS-containing mixture having a reduced hydroxy acetone content can likewise be obtained by means of the process of the invention.

The process of the invention and the apparatus of the invention are shown by way of examples in FIGS. 1 to 6, without the process or the apparatus being restricted to these embodiments.

Figure 1:
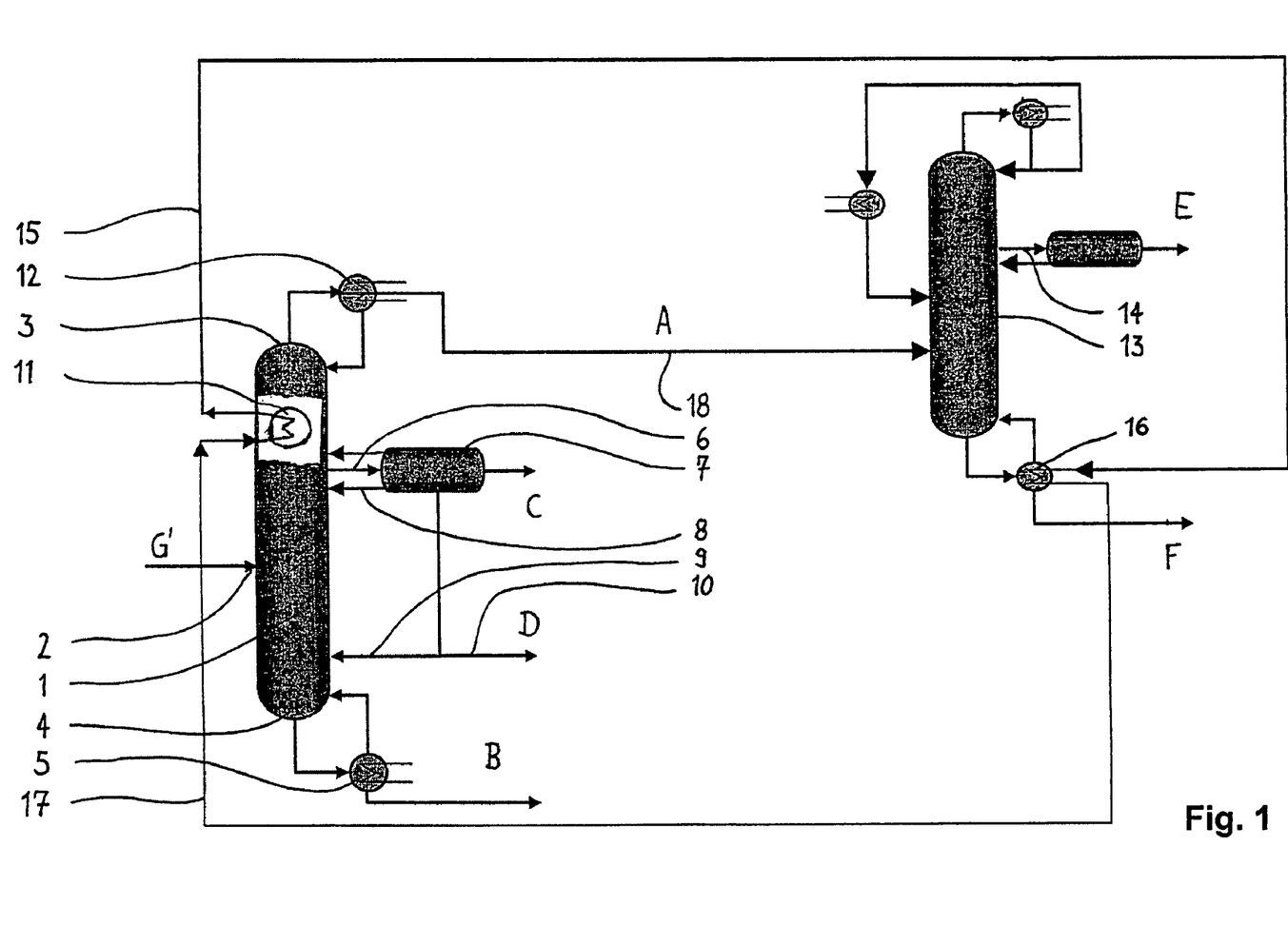
FIG. 1 is a schematic view of a first embodiment of the process and apparatus of the invention.

FIG. 1 schematically shows an embodiment of the process and apparatus of the invention. The apparatus of the invention comprises a distillation column 1 which has a side inlet 2 through which the cleavage product mixture can be fed in for the purpose of separating off the phenol. At the top 3 and at the bottom 4 of the column 1, the first fraction A comprising acetone vapor and the second fraction B comprising phenol, respectively, can be taken off. The distillation column 1 of the apparatus of the invention has, at the bottom 4 of the column, a heat exchanger 5 by means of which appropriate heat energy can be introduced into the column 1.

From a side stream take-off 6, which is arranged above the inlet 2, the third fraction comprising at least cumene, hydroxy acetone and water can be removed and preferably passed through a phase separation apparatus 7. Part of the organic and aqueous phase formed in this phase separation apparatus can be returned to the distillation column via lines 8. The remaining part C of the organic phase, which comprises at least cumene and/or α-methylstyrene, can be passed to further work-up. Part of the aqueous phase D can likewise be returned in liquid or vapor form to the distillation column 1 via line 9. The remaining part of the aqueous phase D can be passed via line 10 to utilization or work-up. The distillation column 1 has further an intermediate heat exchanger 11 arranged within the column 1 above the side stream offtake 6. The intermediate heat exchanger 11 reduces the temperature at the top 3 of the column 1 to preferably less than 65° C., particularly preferably around 55° C. to 60° C. at standard pressure, thereby causing a part of the vapors to condense improving internal reflux. The temperature at the top 3 of the column 1 is always selected so that the temperature at the top 3 is lower than the temperature at the bottom 4. Higher boiling compounds in the column 1 are condensed by the intermediate heat exchanger 11 and, thus, the internal reflux ration of the column 1 is increased. Accordingly, the separation of first fraction A comprising acetone for removal at the top 3 of the column 1 is improved and the column head can be constructed smaller, thus saving monetary investment. More further, a reflux cooler 12 for the first fraction A comprising acetone removed at the top 3 of the column 1 can be selected much smaller than before, thus saving both investment and operating costs and large amounts of cooling water.

The first fraction A comprising acetone vapor removed from the column 1 is passed via line 18 to a purification column 13 for further purification in a known manner by distillation. Pure acetone E may be removed from a side offtake 14 of the column 13. A waste stream F is removed from the bottom of column 13 for dumping or work up.

The hot end of the intermediate heat exchanger 11 in column 1 is connected via line 15 to a bottom heater 16 of the purification column 13 to feed cooling water from the intermediate heat exchanger 11 at a temperature of more than around 65° C. to the heater 16 for heating the bottoms in column 13. The cooling water is returned via return line 17 to the intermediate heat exchanger 11 after passing the heater 16. In a typical industrial process, overhead cooling power at the top 3 of column 1 can be saved in a significant amount and, at the same time, the crude acetone can be completely distillated without steam, which otherwise would be required for heating the bottoms of the purification column 13.

Figure 4:
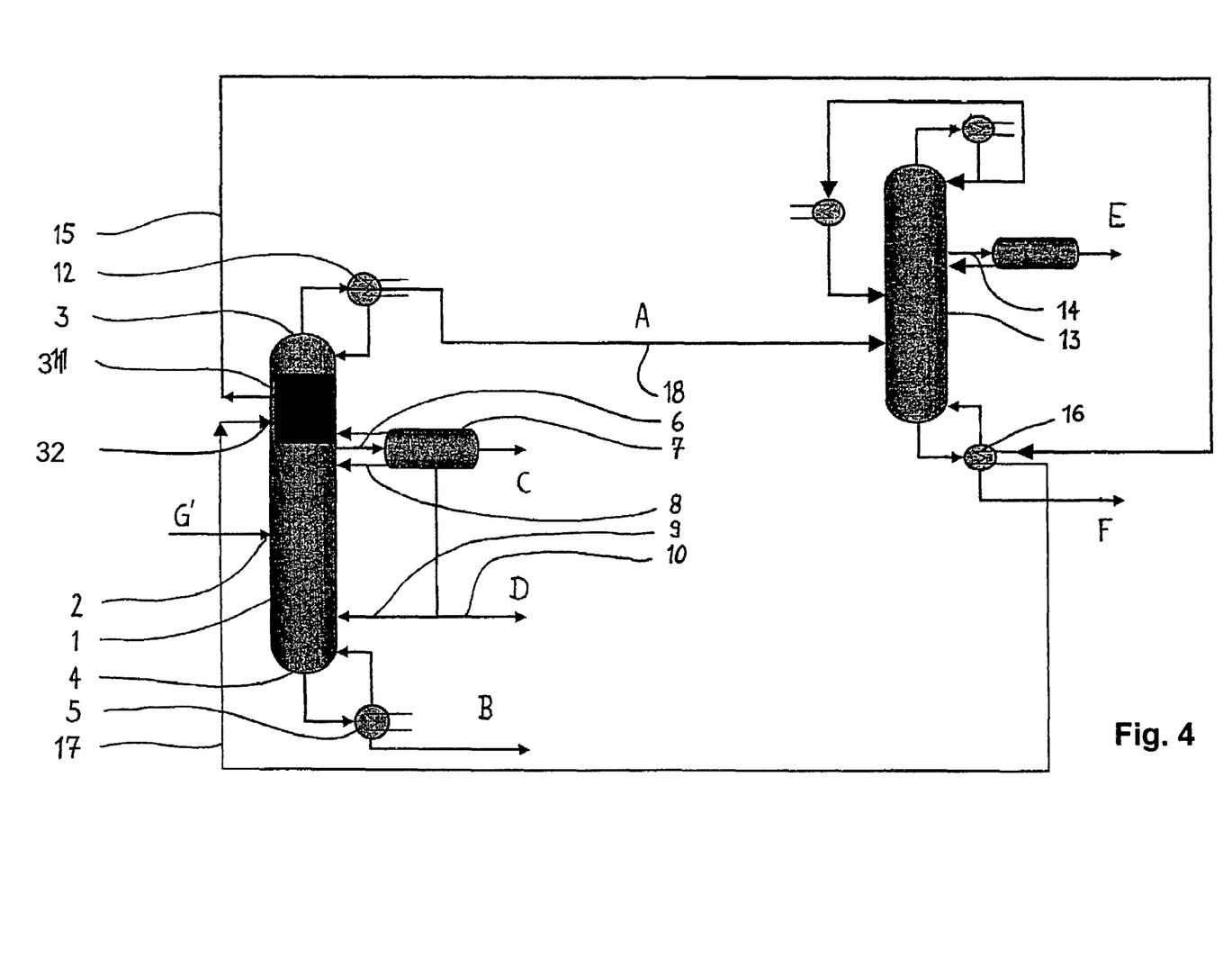
FIG. 4 is a schematic view of a preferred embodiment of the invention.

However, in a preferred embodiment of the invention as shown in FIG. 4, instead of integrating an intermediate heat exchanger 11 in column 1, vapors are directly drawn from the column through side vapor offtake 31 and passed to the bottom heater 16 of the purification column 13. In the heater 16, the vapors from offtake 31 are condensed, thereby heating the bottoms of the purification column 13 most effectively. The condensate is then returned to the distillation column and fed through return side inlet 32. Thus, the energy saving effect of the present invention is believed best. Further, there is no need to provide a large heat exchanger in the upper region of the distillation column 1, may be at approximately 40 meters for an industrial column, where it is hard to reach for maintenance and cleaning. More further, the upper part of the column 1 is significantly simplified and smaller, thus, less expensive, and allowing stronger construction to withstand high wind speeds.

Figure 5:
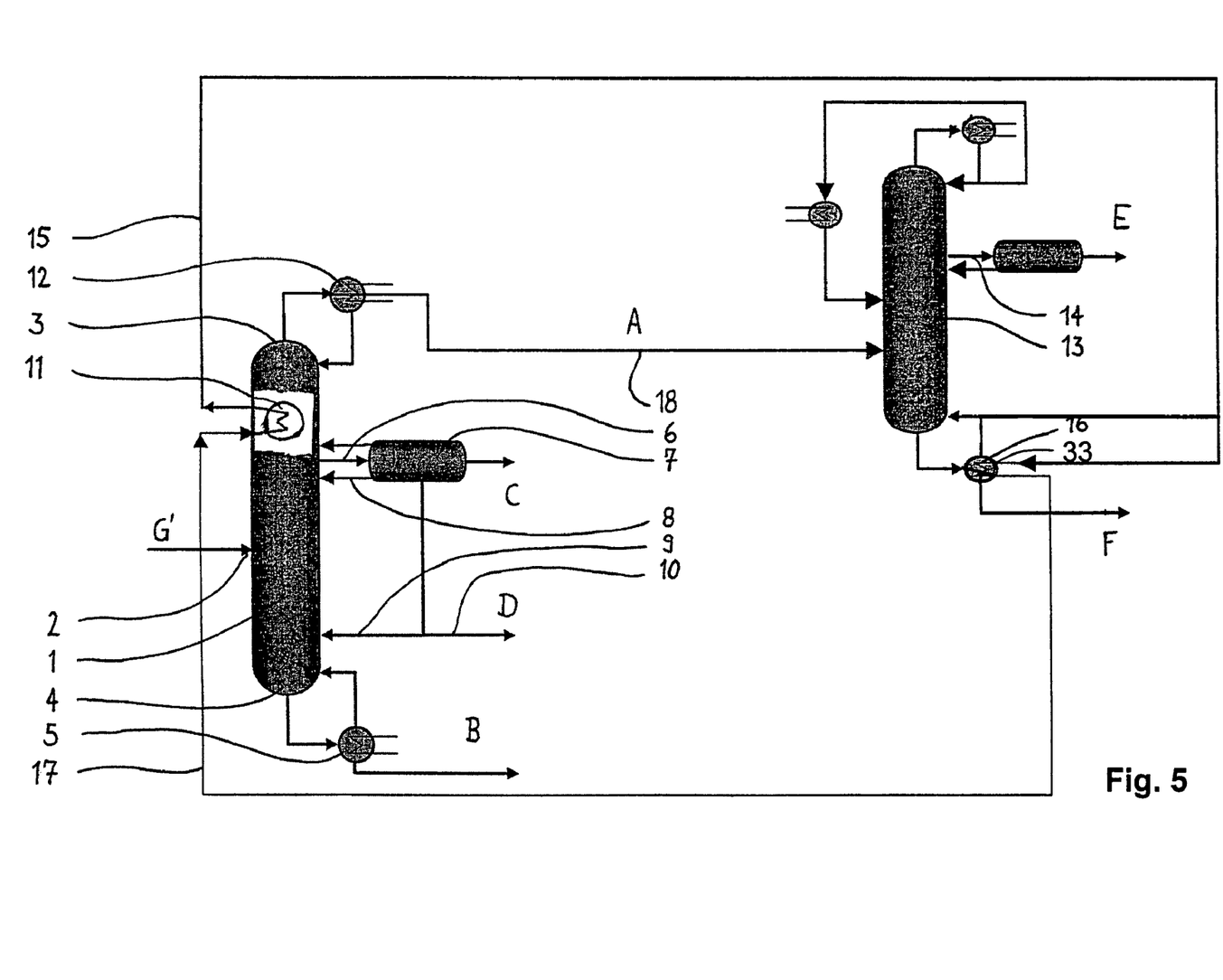
FIG. 5 is a schematic view of an alternative embodiment of the invention.
Figure 6:
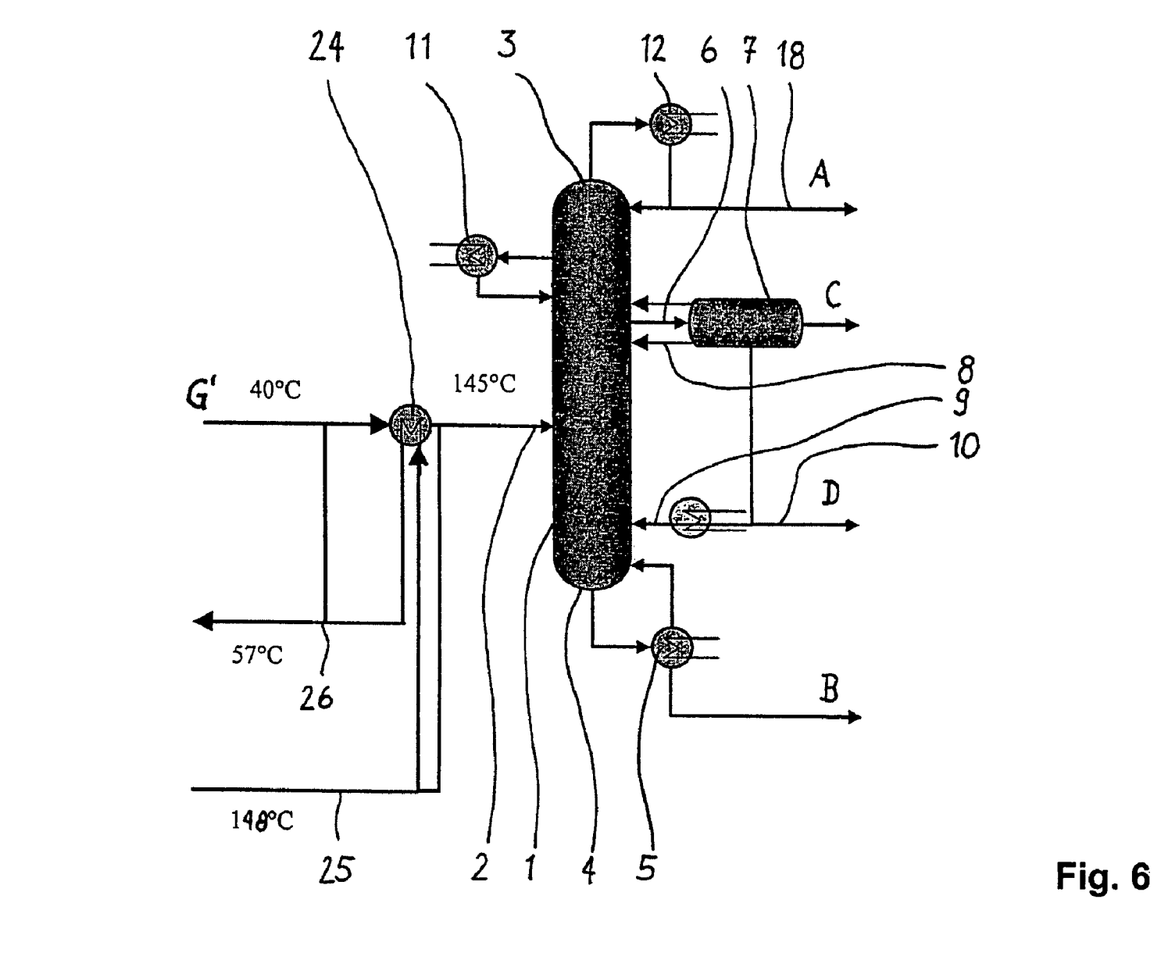
FIG. 6 is a schematic view of a preferred alternative embodiment with respect to the embodiment shown in FIG. 3.

In an alternative embodiment shown in FIG. 5 the condensate from the bottom of the purification column 13 is fed via an optional three way valve 33 or separator for waste stream F, to the cold end of intermediate heat exchanger 11 and returned to the of the purification column 13 after being heated by removing heat from the intermediate heat exchanger 11.

Figure 2:
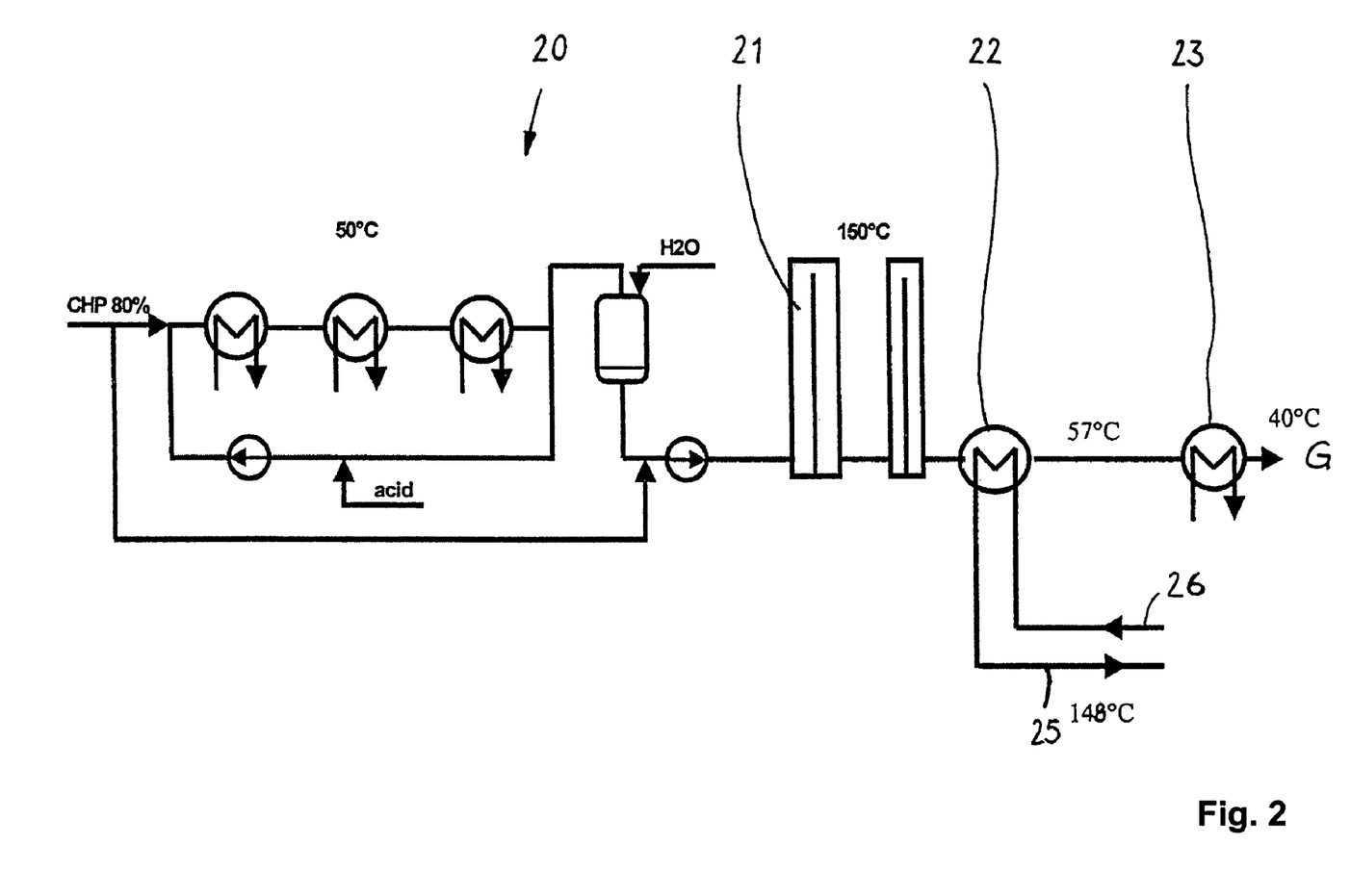
FIG. 2 is a schematic view of another aspect of an embodiment of the invention with respect to thermal after-treatment.

FIG. 2 schematically shows a further embodiment of the process of the invention. A reactor arrangement for a process for the thermal after-treatment of cleavage product from cumene hydroperoxide cleavage as known from DE 100 21 482 A1 and EP 1 151 985 A1 is generally designated by 20. Such a process for the thermal after-treatment of cleavage product from the acid-catalyzed cleavage of cumene hydroperoxide into phenol and acetone in which the cleavage product to be treated thermally is heated in a reactor and in which the heat of reaction of at least one exothermic reaction occurring in this reactor is utilized for heating the cleavage product to be treated thermally in the reactor 21 achieves a high selectivity of the after-treatment combined with a lowering of the energy costs and a higher operating period of the heat exchangers 22 and 23 due to the avoidance of fouling.

The cleavage product mixture G leaves the reactor 21 at a temperature of approximately 150° C. and needs to be cooled to about 40° C. to inhibit the reaction prior neutralization (not shown). Typically, a two step cooling is performed by heat exchangers 22 and 23, wherein the first heat exchanger 22 provides for a significant temperature reduction to about 57° C., and the second heat exchanger 23 to effectively control the temperature of the cleavage product mixture G stream at 40° C.

Figure 3:
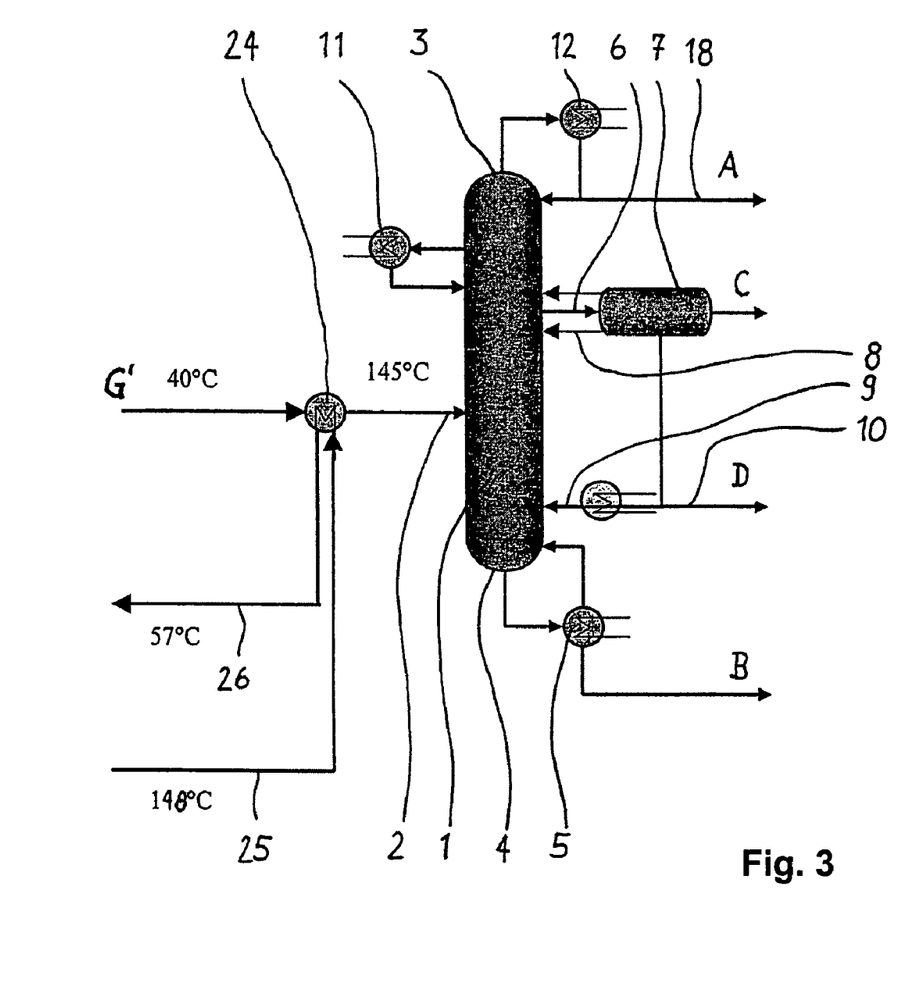
FIG. 3 is a schematic view of an embodiment of the invention using a dedicated preheater.

In the prior art, the heat from heat exchanger 22 was dumped to the environment. According to the invention and as shown in FIG. 3, the heat exchanger is coupled to a preheater 24 upstream of the inlet 2 of column 1, such that hot water or steam from the heat exchanger 22 passes through line 25 at a temperature of approximately 148° C. to the preheater 24. The cold water from the preheater 24 having a temperature of about 57° C. is than directly of indirectly returned through line 26 to heat exchanger 22. Thus, the neutralized cleavage product mixture G' for feeding into column 1 via inlet 2 is preheated to a temperature of about 145° C. Accordingly, the bottoms of column 1 need significantly less energy introduced by heat exchanger 5 to keep the bottoms at a temperature level required for the separation process.

However, it is preferred to directly use the feed stream G' for the distillation column 1 for cooling the cleavage product mixture G stream when leaving the reactor 21. The feed stream G' has, after neutralization and intermediate tank storage for removal of salts and as a production stream buffer, a temperature of typically around or below 40° C. The feed stream G' is directed via line 26 to heat exchanger 22 close to reactor 21 outlet, and removed from the heat exchanger at about 150° C. and fed to the distillation column 1 via line 25 to the side inlet 2 of the distillation column 1. This embodiment provides further improved energy efficiency and use of the heat energy obtainable from the thermal after-treatment in reactor 21.

In a typical industrial process, most of the required cooling power for cooling the cleavage product mixture prior neutralization can be saved, and, at the same time, the feed G' for the distillation column 1 can be significantly preheated without the need of additional steam, which otherwise would be required for additional heating the bottoms of column 1.

What is claimed is:
1. A process for the preparation of phenolic compounds comprising:
   i) oxidizing an alkylaryl compound to produce a cleavage reaction mixture comprising alkylaryl hydroperoxide and the unreacted alkylaryl compound;
   ii) subjecting the product from step i) to a cleavage reaction resulting in a cleavage product mixture comprising at least the phenolic compound, a ketone, the corresponding hydroxy ketone and the unreacted alkyl aryl compound;
   iii) working-up of the cleavage product mixtures from step ii) by distillation, which comprises separating the cleavage product mixture into at least three fractions in a single distillation step by:
      feeding the cleavage product mixture to a distillation column,
      removing a first fraction comprising the ketone at the top of the distillation column,
      removing a second fraction comprising the phenolic compound at the bottom of the distillation column, and
      removing a third fraction comprising unreacted the alkylaryl compound and the hydroxy ketone as side stream, whereby the side stream take-off is situated above the feed of the cleavage product mixture to the distillation column, and
   iv) removing heat from the distillation column, wherein the heat takeoff is situated above the side stream take-off of the third fraction.

2. The process of claim 1, wherein the heat removed from the distillation column is used for heating a second distillation column for obtaining purified ketone from the first fraction.

3. The process as claimed in claim 1, wherein the cleavage reaction mixture is part of the cleavage product mixture obtained from acid-catalyzed cleavage of alkylaryl hydroperoxide.

4. The process as claimed in claim 1, wherein the alkylaryl compound is cumene, the phenolic compound is phenol, the ketone is acetone, and the hydroxy ketone is hydroxy acetone.

5. The process as claimed in claim 1, wherein the cleavage product mixture further comprises water.

6. The process of claim 1, wherein the step of removing heat from the distillation column provides a temperature at the column top of less than 65° C. at standard pressure.

7. The process of claim 6, wherein said temperature at the column top is between about 55° C. to about 60° C. at standard pressure.

8. The process of claim 1, wherein the cleavage product mixture prior feeding into the distillation column is preheated to a temperature of above 70° C. at standard pressure.

9. The process of claim 8, wherein the cleavage product mixture prior feeding into the distillation column is preheated to a temperature of above 100° C. at standard pressure.

10. The process of claim 8, wherein the cleavage product mixture prior feeding into the distillation column is preheated to a temperature of between 110° C. and 180° C. at standard pressure.

11. The process of claim 8, wherein the cleavage product mixture prior feeding into the distillation column is preheated to a temperature of about 140° C. to about 146° C. at standard pressure.

12. A process for separating phenol into at least three fractions in a single distillation step from a cleavage product mixture, said mixture comprising at least acetone, cumene, water and phenol, said process comprising:

feeding the cleavage product mixture to a distillation column through a feed, wherein the cleavage product mixture prior feeding into the distillation column is preheated to a temperature of above 100° C. at standard pressure;

removing a first fraction comprising acetone at the top of the distillation column;

removing a second fraction comprising substituted or unsubstituted phenol at the bottom of the distillation column; and removing a third fraction comprising hydroxy acetone and cumene as side stream through a side-stream take-off, wherein the side stream take-off is situated above the feed of the cleavage product mixture to the distillation column.

13. The process of claim 12, wherein the cleavage product mixture prior feeding into the distillation column is preheated to a temperature of between 110° C. and 180° C. at standard pressure.

14. The process of claim 12, wherein the cleavage product mixture prior feeding into the distillation column is preheated to a temperature of about 140° C. to 146° C. at standard pressure.

15. The process of claim 8, wherein heat energy for the preheating step is obtained from cooling of the cleavage product mixture after thermal after-treatment of the cleavage product mixture from acid-catalyzed cleavage of cumene hydroperoxide prior to neutralization of the cleavage product mixture.

16. The process as claimed in claims 1 or 12, wherein the first fraction comprises at least 75% of a ketone present in the cleavage product mixture before the distillation step.

17. The process as claimed in claims 1 or 12, wherein at least one phenol-containing fraction is obtained containing less than 300 ppm of hydroxy acetone.

18. The process of claim 17, wherein at least one phenol-containing fraction is obtained containing less than 30 ppm of hydroxy acetone.

19. The process of claim 1, further comprising
obtaining a further fraction, said further fraction comprising at least hydroxy acetone, cumene and water, and
separating said fraction into an organic phase and an aqueous phase.

20. The process of claim 19, wherein the organic phase and/or the aqueous phase are returned to the distillation column at least partially.

21. The process as claimed in claims 1 or 12, wherein the cleavage product mixture comprises α-methylstyrene.

22. The process as claimed in claims 1 or 12, wherein the cleavage product mixture has a phenol concentration of from 20 to 90% by weight.

23. The process as claimed in claims 1 or 12, wherein the cleavage product mixture has a hydroxy acetone concentration of from 300 ppm to 5% by weight.

* * * * *

UNITED STATES PATENT AND TRADEMARK OFFICE
CERTIFICATE OF CORRECTION

PATENT NO. : 7,626,060 B2  Page 1 of 1
APPLICATION NO. : 10/888533
DATED : December 1, 2009
INVENTOR(S) : Schwarz et al.

It is certified that error appears in the above-identified patent and that said Letters Patent is hereby corrected as shown below:

Fig. 4, Below Reference Numeral 3, " 3Ⅰ " should be changed to --31--

Column 10, Line 34, "at a side off take" should be changed to --at a side offtake--

Column 10, Line 38, "and an off take" should be changed to --and an offtake--

Column 10, Line 42, "or side off take for" should be changed to --or side offtake for--

Column 10, Line 43, "the side off take" should be changed to --the side offtake--

Column 12, Line 46, "prior neutralization," should be changed to --prior neutralization.--

Column 16, Line 10, "unreacted alkyl aryl" should be changed to --unreacted alkylaryl--

Column 18, Line 11, "further comprising" should be changed to --further comprising:--

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,626,060 B2
APPLICATION NO. : 10/888533
DATED : December 1, 2009
INVENTOR(S) : Christoph Schwarz et al.

It is certified that error appears in the above-identified patent and that said Letters Patent is hereby corrected as shown below:

Title Page,

(*) Notice: Subject to any disclaimer, the term of this patent is extended or adjusted under 35 U.S.C. 154(b) by 588 days.

should read (*) Notice: Subject to any disclaimer, the term of this patent is extended or adjusted under 35 U.S.C. 154(b) by 879 days.

Signed and Sealed this

Tenth Day of August, 2010

David J. Kappos
*Director of the United States Patent and Trademark Office*